(12) United States Patent
Huffman

(10) Patent No.: US 6,471,513 B1
(45) Date of Patent: Oct. 29, 2002

(54) DENTAL MODEL BASE ASSEMBLY

(76) Inventor: Ronald E. Huffman, 725 Country Wood Way, Sapulpa, OK (US) 74066

( * ) Notice: Subject to any disclaimer, the term of this patent is extended or adjusted under 35 U.S.C. 154(b) by 0 days.

(21) Appl. No.: 09/771,772

(22) Filed: Jan. 29, 2001

(51) Int. Cl.$^7$ .................................................. A61C 9/00
(52) U.S. Cl. ........................................... 433/34; 433/74
(58) Field of Search ............................. 433/34, 74, 60, 433/45; 249/54

(56) References Cited

U.S. PATENT DOCUMENTS

| | | |
|---|---|---|
| 921,791 A | 5/1909 | Benson |
| 967,086 A | 8/1910 | Tuttle |
| 1,013,028 A | 12/1911 | Lee |
| 1,745,570 A | 2/1930 | Dimelow |
| 1,772,027 A | 8/1930 | Baumgarten |
| 1,780,117 A | 10/1930 | Craigo |
| 2,031,996 A | 2/1936 | Zelesnick |
| 2,398,671 A | 4/1946 | Saffir |
| 2,585,857 A | 2/1952 | Schwartz |
| 2,842,845 A | 7/1958 | Carlson |
| 3,453,736 A | 7/1969 | Waltke |
| 3,478,428 A | 11/1969 | Stengel |
| 3,518,761 A | 7/1970 | Susman et al. |
| 3,581,398 A | 6/1971 | Thomas |
| 3,934,348 A | 1/1976 | Janjic |
| 3,937,773 A | 2/1976 | Huffman |
| 3,969,820 A | 7/1976 | Kulig et al. |
| 4,021,916 A | 5/1977 | Spalten |
| 4,022,419 A | 5/1977 | Haker |
| 4,116,416 A | 9/1978 | Segura |
| 4,122,606 A | 10/1978 | Roman |
| 4,127,939 A | 12/1978 | Samuel et al. |
| 4,203,219 A | 5/1980 | Wiener |
| 4,240,605 A | 12/1980 | Waltke |
| 4,242,812 A | 1/1981 | Randoll et al. |
| 4,265,619 A | 5/1981 | Lucki et al. |
| 4,283,173 A | 8/1981 | Browne et al. |
| 4,301,357 A | 11/1981 | Huffman |
| 4,359,464 A | 11/1982 | Weinstock |
| 4,371,339 A | 2/1983 | Zeiser |
| 4,378,929 A | 4/1983 | Huffman |
| 4,382,787 A | 5/1983 | Huffman |
| 4,398,884 A | 8/1983 | Huffman |

(List continued on next page.)

FOREIGN PATENT DOCUMENTS

| | | |
|---|---|---|
| DE | 3 436 094 A1 | 10/1984 |
| DE | 3 505 680 A1 | 7/1985 |
| DE | 3 521 137 A1 | 12/1986 |
| DE | 3 825 014 A1 | 1/1990 |
| DE | 295 06 480 U1 | 8/1995 |
| DE | 296 13 916 U1 | 1/1998 |
| EP | 0 210 484 A2 | 2/1985 |
| EP | 0 151 086 A2 | 8/1985 |
| EP | 0 277 026 A2 | 8/1988 |
| EP | 0 291 821 A1 | 11/1988 |
| EP | 0 528 335 A1 | 2/1993 |
| FR | 2 750 851 A1 | 1/1998 |
| FR | 2 770 994 | 5/1999 |
| GB | 866118 | 4/1961 |
| GB | 886118 | 1/1962 |
| WO | WO 88/10101 | 12/1988 |
| WO | WO 01/01881 A2 | 1/2001 |

*Primary Examiner*—Nicholas D. Lucchesi
*Assistant Examiner*—Melba Bumgarner
(74) *Attorney, Agent, or Firm*—Merchant & Gould P.C.

(57) ABSTRACT

A dental model base for supporting a cast dental model where the dental model base has preformed apertures adaptable for securing the dental model to the dental model base and for disengagably retaining a segment of the dental model representing a tooth to be repaired. The preformed apertures are formed through the dental model support surface and a projection extending into a cavity opposite the dental model support surface. The dental model base has a dental model base body which is adaptable for supporting the dental model. The dental model base body may be connected to a disposable articulator or to a metal articulator.

33 Claims, 2 Drawing Sheets

U.S. PATENT DOCUMENTS

| | | | |
|---|---|---|---|
| 4,439,151 A | 3/1984 | Whelan | 433/60 |
| 4,443,192 A | 4/1984 | Blitz | 433/74 |
| 4,449,930 A | 5/1984 | Huffman | 433/64 |
| 4,449,931 A | 5/1984 | Saito | 433/74 |
| 4,459,110 A | 7/1984 | Jackson | 433/74 |
| 4,473,353 A | 9/1984 | Greggs | 433/215 |
| 4,481,162 A | 11/1984 | Huffman | 264/334 |
| 4,494,934 A | 1/1985 | Huffman | 433/213 |
| 4,521,188 A | 6/1985 | Metzler | 433/74 |
| 4,533,323 A | 8/1985 | Huffman | 433/60 |
| 4,538,987 A | 9/1985 | Weissman | 433/60 |
| 4,548,581 A | 10/1985 | Huffman | 433/64 |
| D283,541 S | 4/1986 | Huffman | D24/16 |
| D283,542 S | 4/1986 | Huffman | D24/16 |
| D283,639 S | 4/1986 | Huffman | D24/16 |
| D283,730 S | 5/1986 | Huffman | |
| 4,608,016 A | 8/1986 | Zeiser | 433/74 |
| D286,179 S | 10/1986 | Huffman | D24/10 |
| D286,436 S | 10/1986 | Huffman | D24/10 |
| 4,645,454 A | 2/1987 | Amdur et al. | 433/199.1 |
| D289,924 S | 5/1987 | Huffman | D24/16 |
| 4,671,770 A | 6/1987 | Bell et al. | 433/223 |
| 4,708,648 A | 11/1987 | Weissman | 433/49 |
| 4,708,835 A | 11/1987 | Kiefer | 264/17 |
| 4,721,464 A | 1/1988 | Roden et al. | 433/74 |
| 4,734,033 A | 3/1988 | Huffman | 433/60 |
| 4,767,330 A | 8/1988 | Burger | 433/213 |
| 4,767,331 A | 8/1988 | Hoe | 433/213 |
| 4,834,651 A | 5/1989 | Fenick | 433/74 |
| 4,842,242 A | 6/1989 | Huffman | 249/54 |
| D302,456 S | 7/1989 | Huffman | D24/16 |
| D302,587 S | 8/1989 | Huffman | D24/10 |
| D302,724 S | 8/1989 | Huffman | D24/16 |
| D302,725 S | 8/1989 | Huffman | D24/16 |
| RE33,099 E | 10/1989 | Shoher et al. | 433/222.1 |
| D305,361 S | 1/1990 | Huffman | D24/10 |
| D305,362 S | 1/1990 | Huffman | D24/16 |
| D306,206 S | 2/1990 | Huffman | D24/10 |
| 4,898,359 A | 2/1990 | Gopon | 249/54 |
| 4,917,347 A | 4/1990 | Fenick | 249/54 |
| RE33,271 E | 7/1990 | Shoher et al. | 433/222.1 |
| 4,940,409 A | 7/1990 | Nordin | 433/74 |
| 4,980,124 A | 12/1990 | Dimmer | 419/9 |
| 5,028,235 A | 7/1991 | Smith | 433/223 |
| 5,049,075 A | 9/1991 | Barrut | 433/196 |
| 5,076,789 A | 12/1991 | Tanaka | 433/180 |
| 5,098,290 A | 3/1992 | Honstein et al. | 433/74 |
| 5,197,874 A | 3/1993 | Silva et al. | 433/74 |
| 5,207,574 A | 5/1993 | Garland | 433/74 |
| 5,352,117 A | 10/1994 | Silva | 433/60 |
| 5,393,227 A | 2/1995 | Nooning | 433/74 |
| 5,466,152 A | 11/1995 | Walter | 433/60 |
| 5,470,231 A | 11/1995 | Stern | 433/224 |
| 5,501,600 A | 3/1996 | Johnson | 433/227 |
| 5,622,497 A | 4/1997 | Cho | 433/60 |
| 5,766,007 A | 6/1998 | Huffman | 433/61 |
| 5,769,634 A | 6/1998 | Choi | 433/64 |
| 5,775,899 A | 7/1998 | Huffman | 433/60 |
| 5,788,489 A | 8/1998 | Huffman | 433/60 |
| 5,788,490 A | 8/1998 | Huffman | 433/74 |
| 5,800,166 A | 9/1998 | Huffman | 433/60 |
| 5,807,099 A | 9/1998 | Johnson | 433/25 |
| 5,868,569 A | 2/1999 | Huffman | 433/60 |
| 5,996,963 A * | 12/1999 | Michael | 249/54 |
| D429,815 S | 8/2000 | Huffman | D24/176 |
| D430,672 S | 9/2000 | Huffman | D24/176 |

* cited by examiner

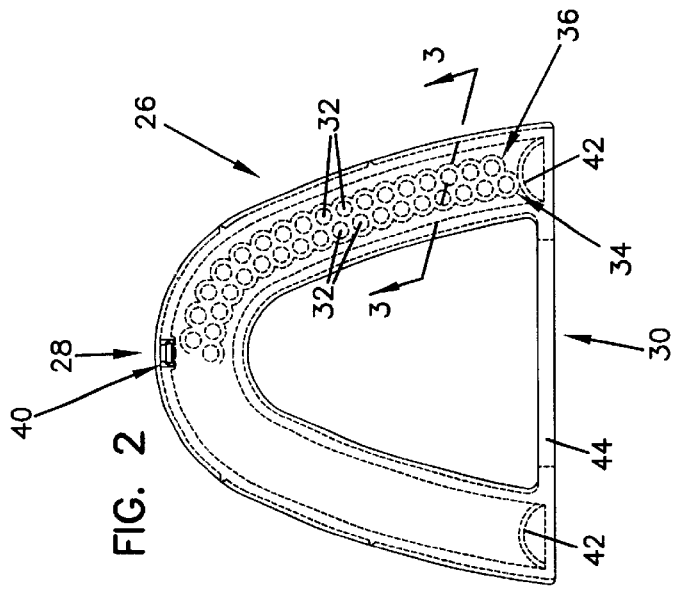
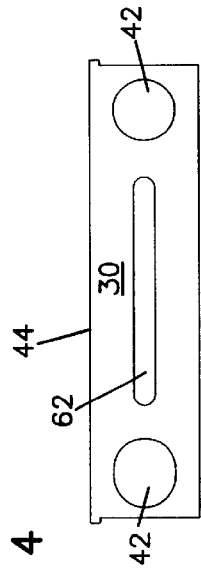
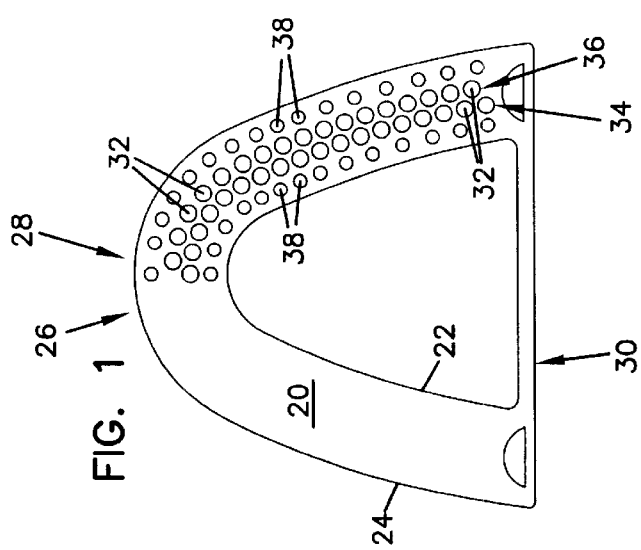
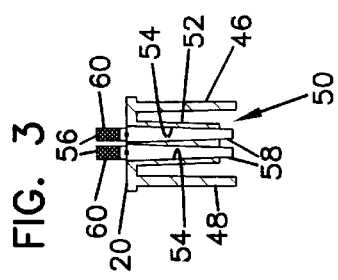

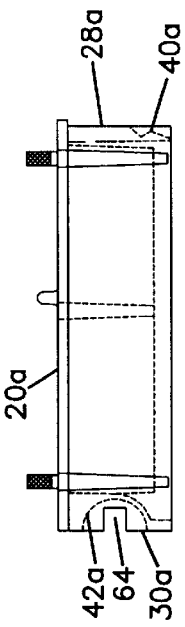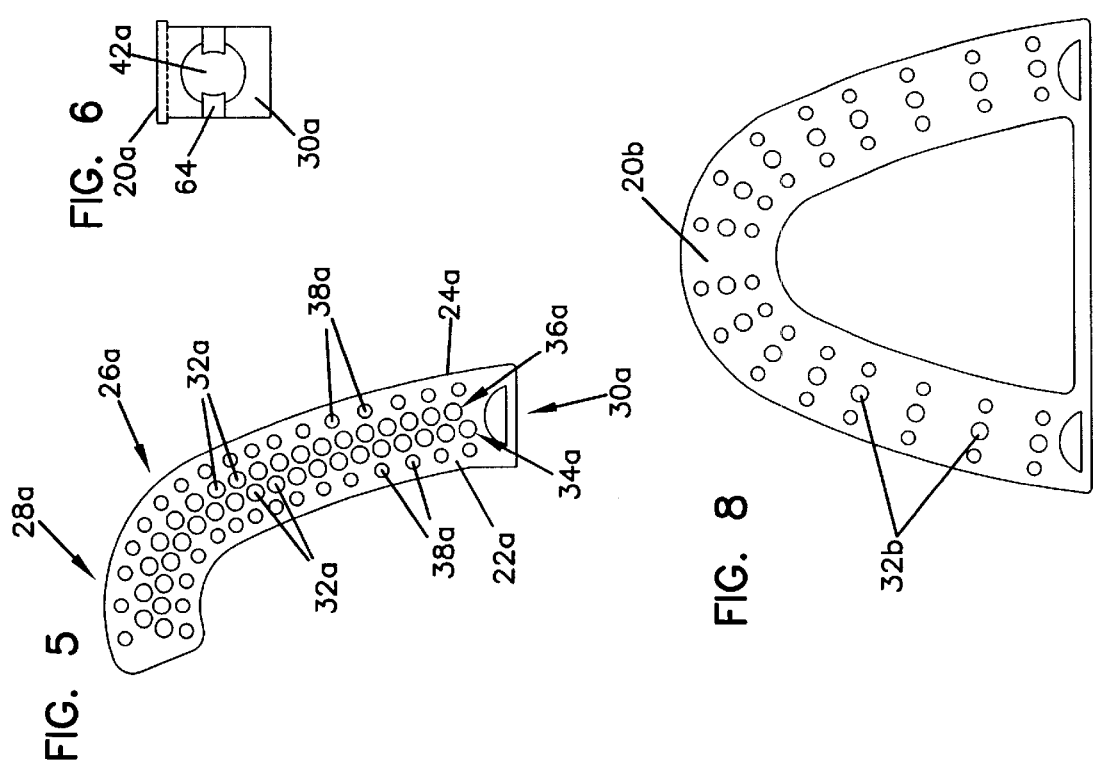

DENTAL MODEL BASE ASSEMBLY

BACKGROUND OF THE INVENTION

This invention relates generally to a dental model base assembly and more particularly to such an assembly in which a dental base body having a plurality of apertures may be attached to a disposable dental articulator or a metal articulator.

Damaged teeth may be repaired or replaced by crowns, bridge inlays or other common dental prosthesis. A successful repair requires accurate alignment and visual uniformity of the repaired tooth with the patient's other teeth. Typically, a model is made of the patient's teeth and the prosthesis is fitted to the model and adjusted to achieve proper alignment and visual uniformity.

The model is typically formed by having a patient bite into a pliant casting material which cures to create a mold cavity having a negative impression of the patient'teeth and gums. The mold can be of all or any portion of the patient'gum line. A castable material is then poured into the negative impression to create a stone replica or dental model of the patient's teeth and gums.

To facilitate prosthesis development, the replica of the damaged tooth or teeth is severed from the remainder of the dental model. Severability is achieved by positioning the knurled end of a tapered dowel pin in the uncured stone material in correspondence with the damaged tooth or teeth. The dowel pin or pins must be carefully aligned and held in position which requires skill and time. Once the casting of the gum and teeth has hardened, the cured dental model is positioned adjacent an uncured dental model base which is held in a dental base mold. The tapered portion of the dowel pins protruding from the dental model are positioned in the uncured dental model base. To prevent bonding with the dental model base, wax may be placed between the base and the dental model and around the tapered portion of the dowel pins.

Once the dental model base has cured a saw cut on each side of the damaged tooth model is made down to the dental model base which allows removal of the damaged tooth model and the attached dowel from the rest of the dental model.

Once the damaged tooth model is removed, the prosthesis can be fitted and adjusted without the spatial limitations encountered when the damaged tooth model is joined to the full dental model. After the prosthesis is made and attached to the dental model segment, the tapered dowel attached to the dental model segment is guided into its respective aperture in the dental model base which guides the dental model segment to its position in the dental model. Alignment and visual conformity are then assessed.

Alignment is ascertained by evaluating the registration of the repaired tooth with the dental model of the patient's opposing teeth. This is achieved by connecting the upper and lower dental model with an articulator. If the prosthesis is out of alignment or does not visually conform to the rest of the patient's teeth, the dental model segment containing the damaged tooth can be removed adjusted and returned to the dental model base. This process is repeated until proper alignment and visual conformity is achieved. Thus, the model of the damaged tooth may be removed and inserted into the base repeatedly. This repeated removal and reinsertion can damage the fit of the tapered portion of the dowel pin within the cast dental model base which decreases the accuracy of the alignment procedure.

The Vertex® articulator is one disposable articulator typically used to check the alignment of repaired teeth. The Vertex® articulator is glued to a slot in the rear portion of the cast dental model bases. Other typical articulators are metal and the dental model is attached semi-permanently by applying a bonding agent, such as plaster, to the dental model base and the articulator. While metal articulators may be separated at the hinge, protruding portions of the articulator obstruct access to the dental model from certain directions. A technician may prefer using one type of articulator in certain circumstances and the other when circumstances are different.

The above described process requires time for the dental model and dental model base castings to cure. Also, skill and time are both required to accurately place the dowel pins in the dental model. Any misalignment may result in an unusable casting. Thus, considerable time is spent achieving proper alignment and allowing the dental model base casting to cure.

Some dental model bases are fabricated from plastic. In one version, a technician must drill a tapered aperture in the dental model base to accommodate the placement of the dowel pin in the dental model casting. Skill and time are required to align the dowel pin with the damaged tooth model and the plastic base and to accurately drill the tapered aperture which receives the tapered dowel pin. Another available plastic dental model base has a plurality of preformed apertures for receiving dowel pins which eliminate the above-mentioned drilling step. However, the apertures are not positioned to correspond with normal tooth placement.

Also, in some existing full arch plastic bases, plastic extends from the right molars to the left molars, creating a platform for excess casting material in the lingual area. It may be desirable to remove this excess casting material as part of the model preparation process. The plastic platform interferes with this removal step. The platform also may hinder assessment of visual conformity.

In summary, the dowel pins may be accurately aligned with the damaged tooth in a cast dental model base; however, the casting procedure takes time and requires skill. Plastic bases avoid the expense of casting a dental model base but may require additional steps, such as drilling, for accurate placement of a dowel within the dental model. If the plastic base has preformed apertures for dowel placement, the apertures often do not correspond to normal tooth placement and skill is required to accurately place the dowels within the dental model. Inaccurate placement of the dowel in a cast or preformed dental model base may result in an unusable dental model as the dental model segment may be unseverable from the dental model.

As mentioned above, brass dowels or pins are typically used to detachably engage a dental model segment to the dental model base. However, brass dowels are undesirable in some circumstances. For example, porcelain facings are often created to repair damaged teeth. The green porcelain material is applied to a damaged tooth model and the dental model segment containing the tooth model is heated to set the porcelain material. This heating temperature is elevated and will adversely affect typical metal dowels.

U.S. Pat. No. 5,788,489 addresses many of the concerns raised above, and is incorporated herein by reference.

SUMMARY OF THE INVENTION

The inventions claimed herein are directed to improvements to prior art dental model bases.

One embodiment has a dental model mounting surface. A wall extends from the second side of the dental model mounting surface. The interior surface of the wall defines a cavity. A plurality of projections extend from the second side of the dental model mounting surface into the cavity.

The projections define a plurality of tapered apertures extending from the first side of the dental model mounting surface.

In another embodiment, a single projection extends into the cavity described above. The projection defines a plurality of tapered apertures extending from the dental model support surface described above.

BRIEF DESCRIPTION OF THE DRAWINGS

FIG. 1 is a top plan view of an embodiment of the present invention.

FIG. 2 is a bottom plan view of an embodiment of the present invention.

FIG. 3 is a section view of an embodiment of the present invention.

FIG. 4 is a rear elevation view of an embodiment of the present invention.

FIG. 5 is a top plan view of an embodiment of the present invention.

FIG. 6 is a rear elevation view of an embodiment of the present invention.

FIG. 7 is a side elevation view of an embodiment of the present invention.

FIG. 8 is a top plan view of an embodiment of the present invention.

FIG. 9 is a bottom plan view of an embodiment of the present invention.

DESCRIPTION OF THE PREFERRED EMBODIMENTS

FIG. 1 depicts a full arch embodiment of one aspect of the present invention. In this embodiment, the dental model support surface 20 has an interior edge 22 and an exterior edge 24. The interior edge 22 defined an unobstructed lingual area. The dental model support surface 20 is the portion of the dental model base 26 adapted to support a dental model. The dental model base 26 has a first end 28 and a second end 30.

A plurality of apertures 32 are formed in the dental model support surface 20. In this embodiment, the apertures 32 form an interior row 34 and an exterior row 36. The apertures of the exterior row 36 are off-set from and adjacent the apertures of the interior row 34. The interior row 34 and the exterior row 36 are positioned to track the normal tooth line of a patient. A plurality of indexing studs 38 are in rows adjacent the interior edge 22 and exterior edge 24.

As shown in FIG. 2, a receiver 40 is at the dental model base first end 28. A pair of hemispheric sockets 42 are at the dental model base second end 30. A bar 44 is interposed between the sockets 42 at the second end 30 of the dental model base 26. In one embodiment, the dental model base 26 is made of a polycarbonate such as Lexan.

FIG. 3 is a cross-section of the dental model base 26. An exterior wall 46 extends from the dental model support surface 20. An interior wall 48 also extends from the dental model support surface 20. A cavity 50 is defined by the interior wall 48, the exterior wall 46 and the dental model support surface 20. A projection 52 extends from the dental model support surface 20 into the cavity 50. Apertures 32 extend through the projection 52 from the dental model support surface 20. The apertures 32 have an interior wall 54. In one embodiment, the majority of the aperture interior wall 54 tapers at a two degree angle relative to the centerline of the aperture 32. In this embodiment, the 0.05 inches of the aperture remote from the dental model support surface 20 is not tapered.

The apertures 32 are adapted to slidingly receive pins 56. Pins 56 have a tapered end 58 and a knurled end 60. In one embodiment, pins 56 are tapered at a two degree angle relative to the centerline of the pin. In one embodiment, the pins 50 are made of stainless steel and have at least a twenty micron finish. The twenty micron finish promotes the sliding engagement of the pin 56 with the aperture 32 and reduces the likelihood a pin 56 will stick to the aperture 32. In one embodiment, the radial dimensional tolerances for the pins 56 are held within 0.005 inches. In one embodiment, the tapered portion of the pins 60 extends beyond the projection 52 into the cavity 50.

FIG. 4 is a view of the dental model base second end 30. The bar 44 has a slot 62 extending along the bar 44 between the hemispheric sockets 42. In one embodiment, the slot 62 extends through the bar. In another embodiment, the slot 62 only extends into the bar 44. In one embodiment, the bar 44 is formed with the dental model base 26. In another embodiment, the bar 44 slidingly engages the dental model base 26 and may be glued to the base 26. In one embodiment, the slot 62 is adapted to receive an articulator attachment tongue. In another embodiment, the hemispheric sockets 42 are adapted to receive a ball connected to an articulator.

FIG. 5 is a view of one embodiment of the present invention adapted for use with a quadrant dental model. FIG. 6 is view of the second end 3 0a of the quadrant dental model base 26a. One hemispheric socket 42a is located at the quadrant dental model second end 30a. In one embodiment, the socket 42a is adapted to receive an articulator ball. A slot 64 is formed across the hemispheric socket 42a. The slot 64 is adapted to receive an articulator attachment tongue.

FIG. 7 is a side view of the quadrant base 26a. The slot 64 is depicted at the second end 30a of the quadrant base 26a. The receiver 40a is at the first end 28a of the quadrant base.

FIG. 8 is a view of one embodiment of the present invention having a single row of apertures 32c in the dental model support surface 20b. The apertures 32b are placed to correspond to the normal position of a patient's teeth. As shown in FIG. 9, a plurality of projections 52b extend into the cavity 50b formed by the exterior wall 46b, the interior wall 48b and the dental model support surface 20b. Tapered apertures 32b extend through the dental model support surface 20b and the projections 52b. The tapered apertures 32b are adapted to slidingly receive a tapered pin as described above.

The dental model base described above may be connected to an articulator through an articulator plate or through the slot at the base's second end as described in co-pending application Ser. No. 09/771,772, entitled Encased Stone Dental Model Base Body.

The foregoing describes various embodiments of the claimed invention. The claimed inventions are not limited to the embodiments described above. Numerous alternative constructions exist that fall within the following claims.

What is claimed is:

1. A dental model base comprising:
    a dental model mounting surface, said dental model mounting surface having a first side and a second side, said first side adapted to be adjacent a dental mold;
    a wall extending from said dental model mounting surface second side, said wall having an interior surface and an exterior surface, said interior surface defining a cavity; and,
    a plurality of projections extending from said dental model mounting surface second side into said cavity, said projections defining a plurality of tapered apertures extending from said dental model mounting surface first side, said apertures adapted to receive a tapered pin.

2. The dental model base of claim 1, wherein:

said apertures are in one-to-one correspondence with normal tooth placement.

3. The dental model base of claim 1, further comprising a tapered pin, wherein:

said tapered pin is stainless steel.

4. The dental model base of claim 3, wherein:

said pin has at least a 20 micron or smaller finish.

5. The dental model base of claim 1, wherein:

said apertures have a two percent taper.

6. The dental model base of claim 1, wherein:

said wall exterior surface having a latch at a first end and a socket at a second end, said latch and socket adapted for receiving an articulator attachment plate.

7. The dental model base of claim 6, wherein:

said wall exterior surface second end has a groove.

8. The dental model base of claim 6 wherein the latch comprises a recessed portion formed in the wall exterior surface.

9. The dental model base of claim 6 wherein the socket comprises an concave-shaped recess formed in the wall exterior surface.

10. The dental model base of claim 6, further comprising an articulator attachment plate, wherein the articulator attachment plate engages the latch and socket to secure the plate to the base.

11. The dental model base of claim 1, wherein:

said base is detachably connectable to an articulator attachment plate.

12. The dental model base of claim 1, wherein:

said base is connectable to an articulator through a ball socket connection.

13. The dental model base of claim 1, wherein:

said base is adapted to support a model of a full dental arch;

said wall exterior surface defining a u-shaped member having an unobstructed lingual area;

said base having a latch at a first end and a socket at a second end; and said base having a groove at said second end.

14. The dental model base of claim 13, wherein:

said base has a pair of sockets at said second end and said groove is interposed between said sockets.

15. The dental model base of claim 14, wherein:

said groove is formed in an articulator attachment bar and said articulator attachment bar is detachably connectable to said dental model base.

16. The dental model base of claim 14, wherein:

said groove is formed in an articulator attachment bar that is integral with said dental model base and is not adapted for detachable connection to said dental model base.

17. The dental model base of claim 1 additionally comprising:

an indexing member on said dental model mounting surface first side.

18. The dental model base of claim 1, wherein:

said exterior wall surface has a socket at second end and said socket is adapted to engage a ball connected to an articulator.

19. A dental model base comprising:

a dental model mounting surface, said dental model mounting surface having a first side and a second side, said first side adapted to be adjacent a dental mold;

a wall extending from said dental model mounting surface second side, said wall having an interior surface and an exterior surface, said exterior surface generally following the contour of a predefined gum line, said interior surface defining a cavity; and, a projection extending from said dental model mounting surface second side into said cavity, said projection defining a plurality of tapered apertures extending from said dental model mounting surface first side, said apertures adapted to receive a tapered pin.

20. The dental model base of claim 19, wherein:

said apertures form two offset rows of apertures and said rows bracket the curvature of a preselected tooth line.

21. The dental model base of claim 19, further comprising a tapered pin, wherein:

said tapered pin is stainless steel.

22. The dental model base of claim 21, wherein:

said pin has at least a 20 micron finish.

23. The dental model base of claim 19, wherein:

said apertures have a two percent taper.

24. The dental model base of claim 19, wherein:

said wall exterior surface having a latch at a first end and a socket at a second end.

25. The dental model base of claim 24, wherein:

said wall exterior surface second end has a groove.

26. The dental model base of claim 19, wherein:

said base is detachably connectable to an articulator attachment plate.

27. The dental model base of claim 19, wherein:

said base is connectable to an articulator through a ball and socket connection.

28. The dental model base of claim 19, wherein:

said base is adapted to support a model of a full dental arch;

said wall exterior surface defining a unshaped member having an unobstructed lingual area;

said base having a latch at a first end and a socket at a second end; and, said base having a groove at said second end.

29. The dental model base of claim 28, wherein:

said base has a pair of sockets at said second end and said groove is interposed between said sockets.

30. The dental model base of claim 28, wherein:

said groove is formed in an articulator attachment bar and said articulator attachment bar is detachably connectable to said dental model base.

31. The dental model base of claim 28, wherein:

said groove is formed in an articulator attachment bar that is integral with said dental model base and is not adapted for detachable connection to said dental model base.

32. The dental model base of claim 19, additionally comprising:

an indexing member on said dental model mounting surface first side.

33. The dental model base of claim 19, wherein:

said exterior wall surface has a socket at second end and said socket is adapted to engage a ball connected to an articulator.

* * * * *

UNITED STATES PATENT AND TRADEMARK OFFICE
CERTIFICATE OF CORRECTION

PATENT NO. : 6,471,513 B1
DATED : October 29, 2002
INVENTOR(S) : Huffman

It is certified that error appears in the above-identified patent and that said Letters Patent is hereby corrected as shown below:

Column 1,
Line 17, "patent' teeth" should read -- patient's teeth --
Line 19, "patient' gum" should read -- patient's gum --

Column 4,
Line 26, "second end 3 O*a*" should read -- second end 30*a* --

Column 6,
Line 22, "a 20 micron" should read -- a 20 micron or smaller --
Line 40, "unshaped" should read -- u-shaped --

Signed and Sealed this

Twenty-ninth Day of July, 2003

JAMES E. ROGAN
*Director of the United States Patent and Trademark Office*